US006224882B1

(12) United States Patent
Smith et al.

(10) Patent No.: US 6,224,882 B1
(45) Date of Patent: May 1, 2001

(54) INSECT CELLS OR FRACTIONS AS ADJUVANT FOR ANTIGENS

(75) Inventors: Gale Eugene Smith, Wallingford; James DeBartolomeis, Madison; Andrei Igorevitch Voznesenski, West Hartford, all of CT (US)

(73) Assignee: Protein Science Corp., Meriden, CT (US)

( * ) Notice: Subject to any disclaimer, the term of this patent is extended or adjusted under 35 U.S.C. 154(b) by 0 days.

(21) Appl. No.: 08/965,698

(22) Filed: Nov. 7, 1997

(51) Int. Cl.$^7$ .......................... A61K 45/00; A61K 39/00; A01N 63/00
(52) U.S. Cl. ................................ 424/279.1; 424/278.1; 424/93.1; 424/184.1
(58) Field of Search ........................... 424/279.1, 278.1, 424/93.1, 184.1

(56) References Cited

U.S. PATENT DOCUMENTS 4,745,051    5/1988   Smith et al. .

FOREIGN PATENT DOCUMENTS 265785      5/1988   (EP) .
0370573     5/1990   (EP) .

OTHER PUBLICATIONS

Menrad, et al. Hybridoma. 16, 465–71, Oct. 1997.*
Nene et al. Infect. Immun. 63, 503–08, Apr. 1995.*
McCown et al. Am J. Trop. Med. Hyg. 42, 491–499, 1990.*
U.S. application No. 07/920,197, Cochran et al., filed Oct. 16, 1986.
Goodman–Snitkoff et al., The Journal of Immunology, vol. 147:410–415 (1991).
Miller et al., J. Exp. Med., vol. 176:1739–1744 (Dec. 1992).
Eldridge et al., Molecular Immunology, vol. 28, No. 3:287–294 (1991).
Todd et al., Vaccine, vol. 15, No. 5:564–570 (1997).
Gupta and Siber, Vaccine, vol. 13, No. 14:1263–1276 (1995).
Richardson, C.D. (editor), Methods in Molecular Biology 39, Humana Press, (1995).
Smith et al., Molecular and Cellular Biology, vol. 3(12):2156–2165 (Dec. 1983).
Pennock et al., Molecular and Cellular Biology, vol. 4(3):399–406 (Mar. 1984).
Kamiya et al., Virus Research, vol. 32:373–379 (1994).
Hulst et al., Journal of Virology, vol. 67, No. 9:5435–5442 (Sep. 1993).
McCown et al., Am. J. Trop. Med. Hyg., vol. 42(5):491–499 (1990).
Putnak et al., Am. J. Trop. Med. Hyg., vol. 45(2):159–167 (1991).
Milstein, Sci. Amer. Vol. 243:66–74 (1980).
Engelhard, V.H., Annu. Rev. Immunol., 1994, vol. 12:181–207.
Bocchia et al., Blood, vol. 85, No. 10, May 15, 1995: pp. 2680–2684.
Jonson et al., Infection and Immunity, May 1992, vol. 60, No. 5 pp. 1845–1853.
Bergstrom et al., Molecular Microbiology (1989), vol. 3(4), 479–486.

* cited by examiner

Primary Examiner—Yvonne Eyler
Assistant Examiner—Lin Sun-Hoffman
(74) Attorney, Agent, or Firm—Frommer Lawrence & Haug LLP; Thomas J. Kowalski

(57) ABSTRACT

Disclosed and claimed is an adjuvant for immunogenic, immunological, antigenic or vaccine compositions. The adjuvant is composed of insect cells or fractions thereof. Disclosed and claimed are also methods for preparing and using the adjuvant and compositions containing the adjuvant. Advantageously, a recombinant baculovirus containing DNA encoding and expressing an epitope of interest or antigen can be infected into insect cells such as insect cells derived from a Lepidopteran species such as *S. frugiperda* for expression, and the infected insect cells or a fraction thereof can be used with the expressed epitope of interest or antigen as an inventive antigen or in an inventive immunological, antigen or vaccine composition.

65 Claims, 2 Drawing Sheets

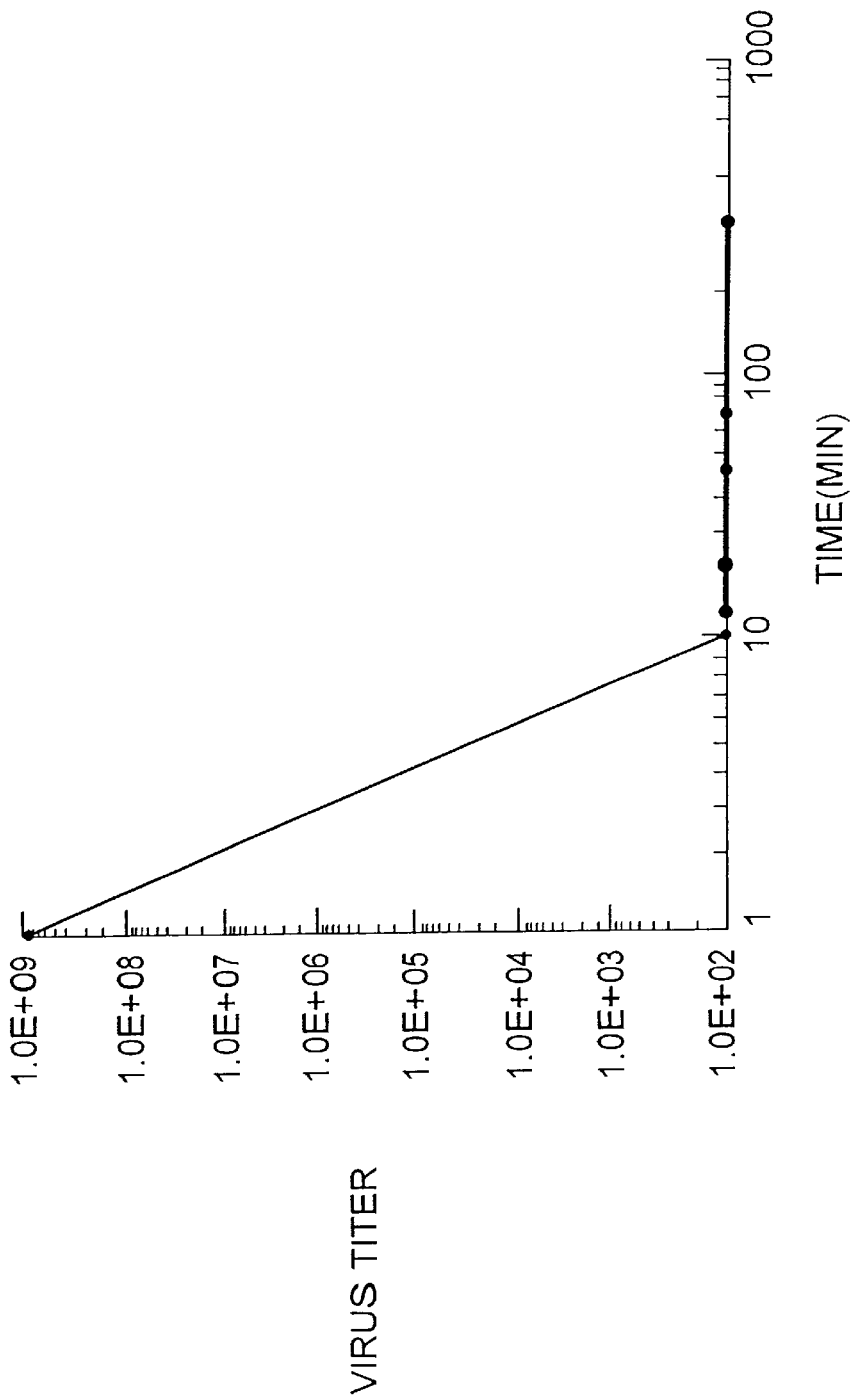

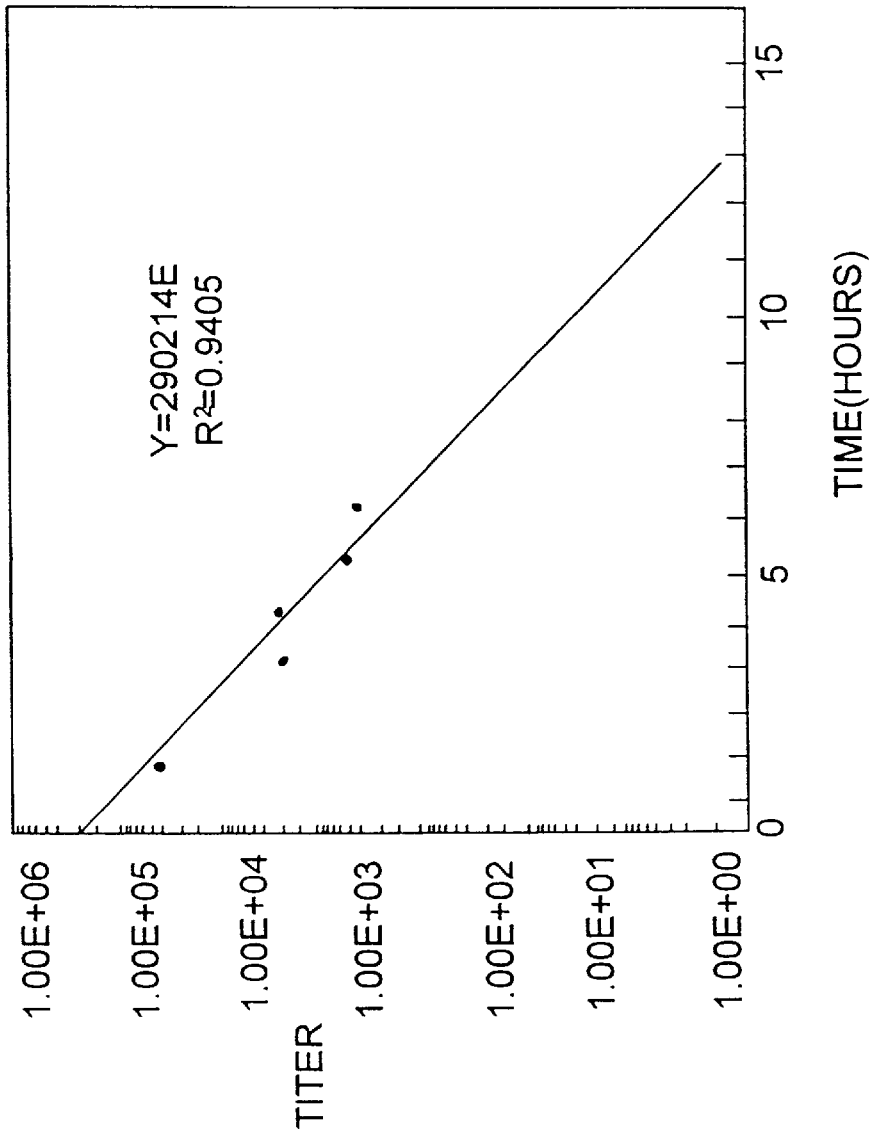

INSECT CELLS OR FRACTIONS AS ADJUVANT FOR ANTIGENS

FIELD OF THE INVENTION

The present invention pertains to adjuvants, such as adjuvants for at least one epitope of interest or antigen (including allergen), immunological, immunogenic, antigenic or vaccine compositions comprising the adjuvants, and methods for making and using the same. More in particular, the present invention relates to insect cells or fractions thereof as adjuvants, such as adjuvants for at least one epitope of interest or antigen (including allergen), immunological, immunogenic, antigenic or vaccine compositions comprising the adjuvants, and methods for making and using the same.

The present invention also relates to insect cells or fractions thereof, e.g., Lepidopteran insect species insect cells or fractions thereof such as S. frugiperda insect cells or fractions thereof, preferably obtainable from infection with an insect virus such as a baculovirus, e.g., a recombinant insect virus such as a recombinant baculovirus, comprising adjuvants, such as adjuvants for at least one epitope of interest or antigen (including allergen), immunological, immunogenic, antigenic or vaccine compositions comprising the adjuvants, and methods for making and using the same.

The at least one epitope of interest or antigen can be a recombinant protein from expression of the recombinant baculovirus. Thus, the invention advantageously pertains to an adjuvant comprising insect cells or fractions thereof, e.g., Lepidopteran insect species insect cells or fractions thereof such as S. frugiperda insect cells or fractions thereof, from infection with a recombinant insect virus such as a recombinant baculovirus, for enhancing the immunogenicity of at least one epitope of interest or antigen (including allergen), to an immunological, immunogenic, antigenic or vaccine composition comprising the adjuvant and the at least one epitope of interest or antigen; wherein, advantageously the epitope of interest or antigen is from expression of at least one exogenous coding nucleic acid therefor by the recombinant virus from infection of the cells by the recombinant virus; and, to methods for making and using the same.

The inventive adjuvants surprisingly favorably alter the immune response by a vertebrate, e.g., avian, mammal, to the epitope of interest or antigen combined therewith. And, the invention pertains to compositions, uses and methods arising from this observation.

Several publications are referenced in this application, either at the end of the specification immediately preceding the claims or where the publication is mentioned; and each of these publications and each of the documents cited in each of these publications is hereby incorporated herein by reference. There is no admission that any of these publications are indeed prior art with respect to the present invention.

BACKGROUND OF THE INVENTION

Immunogenicity can be significantly improved if an antigen is co-administered with an adjuvant, commonly used as 0.001% to 50% solution in phosphate buffered saline. Adjuvants are substances that enhance the immune response to antigens, but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune response to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune response.

Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune response (HIR) and cell-mediated immunity (CMI), immunogens are preferably emulsified in adjuvants.

Chemically defined adjuvants, such as monophosphoryl lipid A, phospholipid conjugates have been investigated (see Goodman-Snitkoff et al., J. Immunol. 147:410–415 (1991)) as has encapsulation of the protein within a proteoliposome (see Miller et al., J. Exp. Med. 176:1739–1744 (1992)).

Synthetic polymers have also been evaluated as adjuvants. These include the homo- and copolymers of lactic and glycolic acid, which have been used to produce microspheres that encapsulate antigens (see Eldridge et al., Mol. Immunol. 28:287–294 (1993)).

Nonionic block copolymers are another synthetic adjuvant being evaluated. Adjuvant effects have also been investigated for low molecular weight copolymers in oil-based emulsions (see Hunter et al., The Theory and Practical Application of Adjuvants (Ed. Stewart-Tull, D. E. S.). John Wiley and Sons, N.Y., pp51–94 (1995)) and for high molecular weight copolymers in aqueous formulations (Todd et al., Vaccine 15:564–570 (1997)).

Desirable characteristics of ideal adjuvants include any or all (preferably most and most preferably all) of:

(1) lack of toxicity;

(2) ability to stimulate a long-lasting immune response;

(3) simplicity of manufacture and stability in long-term storage;

(4) ability to elicit both CMI and HIR to antigens administered by various routes;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example IgA) against antigens.

At this time however, the only adjuvant widely used in humans has been alum. Other adjuvants, such as Sponin, Quil A, and the water-in-oil adjuvant, Freund's with killed tubercle bacilli (Freund's complete) or without bacilli (Freund's incomplete), have had limited use in humans due to their toxic effects; and, concerns have been raised as to undesirable effects in animals. Simply, many adjuvant formulations have been described but most are never accepted for routine vaccines, and few have been evaluated in humans, mainly due to their toxicity.

For example, the mineral oils used as adjuvants in certain animal vaccines are not readily degraded and persist at the site of injection thereby causing unacceptable granulomas; and, in general adjuvant formulations such as mineral compounds oil emulsions, liposomes and biodegradable polymer microspheres cause local reactions due to depot formation at the site of injection.

In fact, the adjuvant effect of most experimental adjuvants has been associated with the adverse effects they elicit.

For instance, adjuvants that act as immunostimulators such as muramyl dipeptide, lipopolysaccaride, lipid A, monophosphoryl lipid A, and cytokines such as IL-2 and IL-12 can also cause systemic side-effects (general toxicity, pyrogenicity), limiting their use.

Accordingly, a problem in the art is a need for adjuvants. There remains a need for improved adjuvants that are safe and economical to manufacture for human and veterinary vaccines (reviewed by Gupta and Siber, Vaccine 13:1263–1276 (1995)).

Insect cells from *S. frugiperda* and other Lepidopteran insect species have been described in the literature and their general use to support the infection and replication of baculoviruses and the production of recombinant proteins is well known (see, e.g., Smith et al., U.S. Pat. No. 4,745,051 (recombinant baculovirus); Richardson, C. D. (Editor), *Methods in Molecular Biology* 39, "Baculovirus Expression Protocols" Humana Press Inc. (1995)); Smith et al., "Production of Human Beta Interferon in Insect Cells Infected with a Baculovirus Expression Vector," Mol. Cell. Biol., 3(12):2156–2165 (1983); Pennock et al., "Strong and Regulated Expression of *Escherichia coli* B-Galactosidase in Infect Cells with a Baculovirus vector," Mol. Cell. Biol., 4(3):399–406. (1984); EPA 0 370 573, U.S. application Ser. No. 920,197, filed Oct. 16, 1986, EP Patent publication No. 265785).

The expression of antigens in insect cells with baculovirus expression vectors and their potential as vaccines is also well known. For example, Kamiya et al., Virus Res. 32:375–379 (1994) relates to the protective effect of glycoproteins of Newcastle disease virus expressed in insect cells following immunization with recombinant glycoproteins. Hulst et al., J. Virol. 67:5435–5442 (1993) pertains to the use of purified recombinant vaccine glycoprotein made in insect cells that protected swine from infection with the hog cholera virus.

There are vaccines where whole insect cells or insect cell membrane fractions containing a selected antigen are used. For example, McCown et al., Am. J. Trop. Med. Hyg. 42:491–499 (1990), use Spodoptera insect whole cells expressing Japanese Encephalitis Virus (JEV) glycoprotein E to immunize and protect mice against JEV. Putnak et al., Am. J. Trop. Med. Hyg. 45:159–167 (1991), use a microsomal membrane fraction of insect cells infected with a baculovirus expressing a Dengue-1 envelope glycoprotein to immunize and protect mice against challenge with Dengue-1 virus.

However, whole insect cell or insect cell membrane fraction vaccines have been a disfavored means for delivering an epitope of interest or antigen; the thinking being that isolation of the epitope of interest or antigen therefrom being necessary for the epitope of interest or antigen to be of practical utility and not just a laboratory curiosity. For instance, insect cell or insect cell membrane fraction vaccines have been used in basic laboratory tests of recombinant expression products with basic laboratory animals, but for the expression products to be considered of practical utility (e.g., useful for human medical or animal veterinary applications), it was believed that the expression products needed to be isolated further from the insect cells or insect cell membrane fractions.

Thus, heretofore there has been no recognition that insect cells or fractions thereof, e.g., Lepidopteran insect species insect cells or fractions thereof such as *S. frugiperda* insect cells or fractions thereof, preferably obtainable from infection with an insect virus such as a baculovirus, e.g., a recombinant insect virus such as a recombinant baculovirus, can be adjuvants, such as adjuvants for at least one epitope of interest or antigen (including allergen), e.g., an epitope of interest or antigen from expression by the recombinant baculovirus.

OBJECTS AND SUMMARY OF THE INVENTION

It has now been surprisingly found that preparations of insect cells such as from the Lepidopteran species, e.g., *Spodoptera frugiperda*, preferably when infected with an insect virus such as a baculovirus, e.g., a baculovirus genetically engineered to produce an epitope of interest or antigen, for instance, by following the methods of Smith et al. (Mol. Cell Biol., 12:2156–2165 (1983)), have the unexpected property of acting as an adjuvant.

The present invention can have any or all as an object: to provide an adjuvant, compositions comprising an adjuvant, methods for making or using an adjuvant or a composition composition comprising an adjuvant.

Accordingly, the present invention provides an adjuvant comprising insect cells or a fraction thereof, advantageously cells from an insect species which is not biting and/or from an insect species wherein hypersensitivity to the insect cell antigens is low or absent in human and animal species and/or from an insect species which is non-toxic, non-pyrogenic, non-tumorgenic, contain no known retroviruses or other human or animal viruses, mycoplasma or other pathogens, for instance, Lepidopteran species, e.g., *Spodoptera frugiperda* such as the Sf9 cell line. More advantageously, the insect cells or fraction thereof are obtainable from infection of the cells by an insect virus, such as a baculovirus, and, preferably the insect cells or fraction thereof are from infection of the cells by an insect virus. In an embodiment, the insect virus can be a recombinant virus; for instance a recombinant baculovirus. The recombinant insect virus can comprise at least one exogenous coding nucleic acid, e.g., DNA, for an epitope of interest or antigen.

The invention further provides an immunogenic, immunological, antigenic or vaccine composition comprising the inventive adjuvant. The composition can also comprise at least one epitope of interest or antigen. Accordingly, the invention can provide an immunogenic, immunological, antigenic or vaccine composition comprising at least one epitope of interest or antigen and insect cells or a fraction thereof, as adjuvant.

The insect cells are preferably from a Lepidopteran species, e.g., *Spodoptera frugiperda*; and, are advantageously obtainable, and preferably obtained, from infection of such cells by an insect virus such as a baculovirus, e.g., a recombinant insect virus for instance a recombinant baculovirus.

The epitope of interest or antigen can be from any source, e.g., native expression by a pathogen, recombinant expression, etc. and combinations thereof. The epitope of interest or antigen can have been isolated from its source, and added to insect cells or a fraction thereof. Alternatively or additionally, the epitope of interest or antigen can be from expression by a recombinant insect virus, such as a baculovirus, used to prepare the adjuvant.

Thus, the invention provides an immunogenic, immunological, antigenic or vaccine composition comprising at least one recombinant epitope of interest or antigen from expression of an insect virus having infected an insect cell and the insect cell or a fraction thereof as adjuvant. The virus is preferably a baculovirus and the insect cell is preferably from a Lepidopteran species, e.g., *Spodoptera frugiperda*. The composition can additionally contain at least one epitope of interest or antigen isolated from its source and added to the adjuvant.

Accordingly, the invention comprehends multivalent or combination or "cocktail" compositions, e.g., obtainable from adding isolated epitopes or antigens to the adjuvant; or from adding at least one isolated first epitope of interest or antigen to a composition comprising at least one second epitope of interest or antigen and insect cells or a fraction thereof as adjuvant, wherein the at least one second epitope of interest or antigen is the same as or different from the first and is obtainable and preferably obtained from expression by a recombinant insect virus, e.g., expression of at least one exogenous coding nucleic acid by the recombinant insect virus, from infection of the insect cells.

The invention still further provides a kit for an immunogenic, immunological, antigenic or vaccine composition comprising a insect cells or a fraction thereof as adjuvant and at least one epitope of interest or antigen, and optionally instructions for admixing or combining the adjuvant and epitope of interest or antigen and/or administering the composition. The adjuvant and at least one epitope of interest can be in separate containers, which containers can be packaged together.

Since in an advantageous embodiment the insect cell or fraction thereof can be used as an adjuvant in a multivalent or combination or "cocktail" composition, the kit can comprise at least one isolated first epitope of interest or antigen, and at least one second epitope of interest or antigen and insect cells or a fraction thereof as adjuvant, wherein the at least one second epitope of interest or antigen is the same as or different from the first and is obtainable and preferably obtained from expression by a recombinant insect virus, e.g., expression of at least one exogenous coding nucleic acid by the recombinant insect virus, from infection of the insect cells, and optionally instructions for admixing or combining the adjuvant and epitope of interest or antigen and/or administering the composition; and, the at least one second epitope of interest or antigen and adjuvant can be in a first container and the at least one epitope of interest can be in a second container, which containers can be packaged together.

The invention further comprehends a method for preparing an adjuvant comprising isolating insect cells, or fractions thereof, e.g., fractions obtainable mechanical and/or chemical disruption; for instance, isolating insect cells and then isolating fractions thereof. The insect cells are preferably from a Lepidopteran species, e.g., *Spodoptera frugiperda*; and, are advantageously obtainable, and preferably obtained, from infection of such cells by an insect virus such as a baculovirus, e.g., a recombinant insect virus for instance a recombinant baculovirus. When obtained from infection of such cells by an insect virus, it is advantageous to remove or inactivate the virus. Mechanical and/or chemical means can be used to remove or otherwise inactivate the virus. The insect cells can also be fractionated into a membrane fraction comprising the at least one epitope of interest or antigen from recombinant expression, and that membrane fraction can comprise the adjuvant (as well as a composition comprising the adjuvant and at least one epitope of interest or antigen).

The invention further comprehends a method for preparing an immunological, immunogenic, antigenic or vaccine composition comprising: isolating at least one epitope of interest or antigen from expression thereof by a recombinant insect virus such as a recombinant baculovirus in insect cells, preferably from a Lepidopteran species, e.g., *Spodoptera frugiperda*, together with the insect cells or a fraction thereof. Additionally or alternatively, the invention comprehends a method for preparing an immunological, immunogenic, antigenic or vaccine composition comprising admixing at least one epitope of interest or antigen with isolated insect cells or a fraction thereof, preferably from a Lepidopteran species, e.g., *Spodoptera frugiperda*, advantageously obtainable from infection thereof by an insect virus such as a baculovirus, and more advantageously obtainable from infection thereof by a recombinant insect virus.

The invention even further still comprehends uses of the adjuvants and of the immunological, immunogenic, antigenic or vaccine compositions. For instance, use of insect cells or fractions thereof to enhance the immunogenicity of at least one epitope of interest or antigen, e.g., the invention comprehends a method for enhancing the immunogenicity of at least one epitope of interest or antigen comprising administering an adjuvant comprising insect cells or fractions thereof, preferably from a Lepidopteran species, e.g., *Spodoptera frugiperda*, advantageously obtainable from infection thereof by an insect virus such as a baculovirus, and more advantageously obtainable from infection thereof by a recombinant insect virus.

The administering can be contemporaneous, e.g., the at least one epitope of interest or antigen is in the same composition as the adjuvant and the administering is of the composition. In this respect the adjuvant is administered "with" the epitope of interest or antigen.

Or, the administering can be sequential, e.g., the at least one epitope of interest or antigen is administered in such a manner either prior to or after the administration of the adjuvant so as to have immunogenicity enhanced thereby (for instance, epitope of interest or antigen administered in same manner such as subcutaneously and in the same location of the host such as arm or buttocks as adjuvant and epitope of interest or antigen administered either prior to or after the adjuvant but within such a time period that the adjuvant enhances the immunogenicity of the epitope of interest or antigen). In this respect the adjuvant is administered "in conjunction with" the epitope of interest or antigen.

The invention thus further provides a method for obtaining an immunological, immunogenic, antigenic or protective response in an animal such as vertebrate host, e.g., avian, mammalian, human host, advantageously an enhanced response, comprising administering an inventive immunological, immunogenic, antigenic or vaccine composition, or an inventive adjuvant composition. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

These and other embodiments are disclosed or are obvious from and encompassed by, the following Detailed Description.

BRIEF DESCRIPTION OF FIGURES

The following Detailed Description, given by way of example, but not intended to limit the invention to specific embodiments described, may be understood in conjunction with the accompanying Figures, incorporated herein by reference, in which:

FIG. 1 shows a graph of baculovirus inactivation (virus titer (1.0 E+2 to 1.0 E+9) vs. time (min)) by chemical inactivation (SDS/cholate treatment); and, FIG. 2 shows a graph of baculovirus inactivation (virus titer (1.0 E+0 to 1.0 E+6) vs. time (hours)) by chemical inactivation (formaldehyde treatment) showing that inactivation follows first order kinetics.

DETAILED DESCRIPTION

As discussed above, the present invention provides, inter alia, an adjuvant, compositions comprising the adjuvant and optionally at least one eptiope of interest or antigen, a kit comprising the adjuvant, uses for the adjuvant, the compositions, the kits, and methods for making and using the adjuvants, composition, and kits.

Thus, in an embodiment the invention provides a pharmaceutical preparation for administration in vivo to effect immunization is comprised of whole insect cells, disrupted insect cells or fractions of insect cells and optionally at least one epitope of interest or antigen. Cells, and fractions thereof, from the Lepidopteran species (e.g., butterflies and moths), like those from the fall army worm *S. frugiperda*, especially such cells in combination with an insect virus such as the baculovirus vector used to express an epitope of interest or antigen, have properties that make them suitable for use in pharmaceutical compositions for human and animal use.

*S. frugiperda* insect cells are non-toxic, non-pyrogenic, non-tumorgenic, contain no known retroviruses or other human or animal viruses, mycoplasma or other pathogens. The insect species from which the cells are derived are not biting and hypersensitivity to the insect cell antigens is low or absent in human and animal species.

Also, the present invention provides a method where the adjuvant from the insect cells is a part of a pharmaceutical composition with a selected antigen without the addition of chemicals and without the need for costly formulation steps. Such an adjuvant composition allows for a reduction in the dose of epitope or antigen needed for a desired response such as a protective immunization. This means that vaccines could be less expensive to produce; and thus the invention provides an economic benefit in the production of vaccines which is especially relevant to human vaccines for developing countries and for veterinary vaccines.

The present invention also provides a method of preparing a pharmaceutical preparation comprising at least one epitope of interest or antigen and whole insect cells or disrupted insect cells or fractions of insect cells, for use as a vaccine is described. The at least one epitope of interest or antigen is preferably in contact with the insect cells or disrupted insect cells or fractions thereof. In a preferred embodiment of the invention a nucleic acid molecule encoding the epitope of interest or antigen, e.g., a gene is cloned into a baculovirus expression vector, such as the *Autographa californica* Multiple Nuclear Polyhedrosis Virus (AcMNPV) preferably under the control of a promoter such as a strong promoter, e.g., the polyhedrin promoter (Smith et al., supra). The selected baculovirus expression vector is then used to infect insect cells that are susceptible to infection by AcMNPV, such as a cell line derived from *S. frugiperda*. Following infection of the insect cells and expression of the selected gene product, the cells containing the recombinant epitope of interest or antigen are collected and used in a pharmaceutical preparation for administration of the epitope of interest or antigen.

In one embodiment of the invention, the insect cells containing the epitope of interest or antigen are separated from the growth medium and used in a suitable pharmaceutical formulation as an immunological, immunogenic, antigenic or vaccine composition.

In a second embodiment of the invention the insect cells containing the epitope of interest or antigen are treated by mechanical or chemical methods or by a combination of mechanical and chemical methods that render the baculovirus non-infectious, do not destroy the adjuvant property of the insect cells, and does not denature that selected antigen.

In a third embodiment of the invention the insect cells containing the epitope of interest or antigen are fractionated into subcellular components, which contain the selected antigen. By way of example, the present invention provides a method to prepare an immunological, immunogenic, antigenic or vaccine composition from *S. frugiperda* insect cells infected with a baculovirus that expresses the antigen, influenza hemagglutinin.

A method is also provided for preparing a pharmaceutical immunological, immunogenic, antigenic or vaccine composition against an avian influenza that induces high levels of antibodies that neutralize an avian influenza virus. Examples of chemical methods are described that inactivate the recombinant baculovirus with which the *S. frugiperda* cells are infected for expression of the epitope of interest or antigen. For instance, formaldehyde at 0.001% to 1.0% concentration can be used to inactivate the baculovirus. Alternatively or additionally a detergent or mixture of detergents can be used to inactivate the baculovirus, e.g., cholic acid (cholate) and/or SDS (sodium dodecyl sulfate) and/or cetyldimethylammonium bromide (CDAB) such as 1–3% preferably 2% cholic acid and/or 0.1–1.0% preferably 0.5% SDS and/or 0.5–1.5% preferably 1% CDAB.

In another example, *S. frugiperda* insect cells infected with a recombinant baculovirus that expresses an epitope of interest or antigen are fractionated into a membrane preparation containing the epitope of interest or antigen for use in an immunological, immunogenic, antigenic or vaccine composition. Other fractions of insect cells such as the cytosol, micorosomal membranes, and nuclei could also be prepared using methods well know to those skilled in the art of cell biology, without any undue experimentation.

An inserted nucleic acid molecule, e.g., the foreign gene, the heterologous or exogenous nucleic acid molecule, for instance, DNA, in an insect virus vector, e.g., in a baculovirus vector, used in the practice of the instant invention, preferably encodes an expression product comprising at least one epitope of interest or antigen (including allergen). Similarly, compositions of the invention can include at least one epitope of interest or an antigen. With respect to these terms, reference is made to the following discussion, and generally to Kendrew, *The Encyclopedia Of Molecular Biology*, Blackwell Science Ltd., 1995 and Sambrook, Fritsch and Maniatis, *Molecular Cloning, A Laboratory Manual*, 2nd Ed., Cold Spring Harbor Laboratory Press, 1982 ("Maniatis et al., 1982").

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, or from another antigen or toxin which elicits a response with respect to the pathogen or toxin, such as, for instance: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nucleoprotein (NP) or an avian influenza hemagglutinin such as influenza A/Jalisco/95 H5 hemagglutinin; a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; a rous associated virus antigen such as RAV-1 env; matrix and/or preplomer of infectious bronchitis virus; a Herpesvirus glycoprotein, e.g., a glycoprotein, for instance from feline herpesvirus, equine herpesvirus, bovine herpesvirus, pseudorabies virus, canine herpesvirus, HSV, Marek's Disease Virus, herpesvirus of turkeys (HVT) or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; a poxvirus antigen, e.g., an ectromelia antigen, a canary pox virus antigen or a fowl pox virus antigen; or an infectious bursal disease virus antigen, e.g., VP2, VP3, VP4.

An epitope of interest can be from an antigen of a human pathogen or toxin, or from another antigen or toxin which elicits a response with respect to the pathogen or toxin, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a *C. tetani* antigen; a mumps antigen; a pneumococcal antigen, e.g., PspA; a Borrelia antigen, e.g., OspA, OspB, OspC of Borrelia associated with Lyme disease such as *Borrelia burgdorferi, Borrelia afzelli* and *Borrelia garinii*; a chicken pox (varicella zoster) antigen; or a Plasmodium antigen.

Of course, the foregoing lists are intended as exemplary, as the epitope of interest can be derived from any antigen of any veterinary or human pathogen or toxin; and, to obtain an epitope of interest, one can express an antigen of any veterinary or human pathogen or toxin.

In regard to the foregoing lists, with respect to Borrelia DNA, reference is made to U.S. Pat. No. 5,523,089; WO93/08306; PCT/US92/08697; Bergstrom et al., Mol. Microbiol., 3(4):479–486 (April 1989); Johnson et al., Infect. and Immun. 60:1845–1853 (1992); Johnson et al., Vaccine 13(12): 1086–1094 (1995); "The Sixth International Conference on Lyme Borreliosis: Progress on the Development of Lyme Disease Vaccine," Vaccine, 13(1):133–135, 1995 and PCT publications WO 90/04411, WO 91/09870, WO 93/04175, and 96/06165.

With respect to pneumococcal epitopes of interest, reference is made to Briles et al. WO 92/14488.

With regard to influenza epitopes of interest and antigens, e.g., HA, and recombinant baculovirus expression thereof, useful in the practice of the present invention, reference is made to Smith et al., U.S. application Ser. Nos. 08/120,601, filed Sep. 13, 1993 (allowed) and 08/453,848, filed May 30, 1995.

With respect to tumor viruses reference is made to *Molecular Biology of Tumor Viruses, RNA TUMOR VIRUSES* (Second Edition, Edited by Weiss et al., Cold Spring Harbor Laboratory 1982) (e.g., page 44 et seq.—Taxonomy of Retroviruses), incorporated herein by reference.

With respect to DNA encoding epitopes of interest, attention is directed to documents cited herein, see, e.g., documents cited supra and documents cited infra, for instance: U.S. Pat. Nos. 5,174,993 and 5,505,941 (e.g., rabies glycoprotein (G), gene, turkey influenza hemagglutinin gene, gp51,30 envelope gene of bovine leukemia virus, Newcastle Disease Virus (NDV) antigen, FeLV envelope gene, RAV-1 env gene, NP (nucleoprotein gene of Chicken/Pennsylvania/1/83 influenza virus), matrix and preplomer gene of infectious bronchitis virus; HSV gD); U.S. Pat. No. 5,338,683 (e.g., DNA encoding Herpesvirus glycoproteins, inter alia); U.S. Pat. No. 5,494,807 (e.g., DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, *C. tetani*, avian influenza, mumps, NDV, inter alia); U.S. Pat. No. 5,503,834 (e.g., Morbillivirus, e.g., measles F, hemagglutinin, inter alia); U.S. Pat. No. 4,722,848 (e.g., HSV tk, HSV glycoproteins, e.g., gB, gD, influenza HA, Hepatitis B, e.g., HBsAg, inter alia); U.K. Patent GB 2 269 820 B and U.S. Pat. No. 5,514,375 (e.g., flavivirus structural proteins); WO 92/22641 (e.g., Lentivirus antigens such as immunodeficiency virus antigens, inter alia); PCT publications WO 93/03145 (e.g., IBDV antigens, inter alia) and WO 94/16716 (e.g., cytokine and/or tumor associated antigens, inter alia); U.S. Pat. No. 5,529,780 (e.g., canine herpesvirus antigens), PCT publication WO 96/3941 (e.g., cytomegalovirus antigens), and PCT/US94/06652 (Plasmodium antigens).

As to antigens for use in vaccine or immunological, immunogenic or antigenic compositions, reference is made to the documents cited herein and the discussion set forth herein (see, e.g., documents cited supra) and also Stedman's Medical Dictionary (24th edition, 1982), e.g., definition of vaccine (for a list of antigens used in vaccine formulations; such antigens or epitopes of interest from those antigens can be used in the invention, as either an isolated product employed with an inventive adjuvant or an expression product of a recombinant insect virus or vector).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology* (Blackwell Scientific Publications, Oxford, 1988).

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD8+ T cell response (which recognizes virus infected cells or cancerous cells). A minimum peptide length of 13 to 25 amino acids is useful to stimulate a CD4+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three-dimensional protein. Janis Kuby, *Immunology*, pp. 79–80 (W. H. Freeman, July 1992).

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, p. 81 (W. H. Freeman, July 1992).

Yet another method for determining an epitope of interest is to perform an X-ray crystallographic analysis of the antigen (full length)-antibody complex. Janis Kuby, *Immunology*, p.80 (W. H. Freeman, July 1992).

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

Some guidelines in determining whether a protein is an epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules,* Blood 85(10):2680–2684, May 15, 1995; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

Accordingly, without any undue experimentation, the present invention can be practiced for any desired epitope of interest or antigen of any human or veterinary pathogen or toxin.

An immunological composition elicits an immunological response—local or systemic. The response can, but need not be protective. An immunogenic composition likewise elicits a local or systemic immunological response which can, but need not be, protective. An antigenic composition similarly elicits a local or systemic immunological response which can, but need not be, protective. A vaccine composition elicits a local or systemic protective response. Accordingly, the terms "immunological composition" and "immunogenic composition" and "antigenic composition" include a "vaccine composition" (as the three former terms can be protective compositions).

An inventive composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. The effective dosage and route of administration are determined by the nature of the composition, e.g., immunogenic, antigenic, immunological or vaccine, as well as by the nature of the epitope of interest or antigen present, by expression level if the recombinant virus is directly used, and by known factors, such as breed or species, age, sex, weight, condition and nature of host, as well as $LD_{50}$ and other screening procedures which are known and do not require undue experimentation. Dosages of epitope of interest or antigen can range from a few to a few thousand, e.g., 10 to 1000 units, or a few to a few hundred micrograms, e.g., 5 to 500 $\mu$g. The recombinant virus or vector can be infected into insect cells in any suitable amount to achieve expression at these dosage levels. Suitable amounts can be an amount of about at least $10^{3.5}$ pfu; e.g., about $10^4$ pfu to about $10^6$ pfu, about $10^4$ pfu to about $10^{10}$ pfu, for instance, about $10^5$ pfu to about $10^9$ pfu, or about $10^6$ pfu to about $10^8$ pfu.

The administration procedure for the inventive compositions of the invention such as immunological, antigenic or vaccine compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions can be prepared in accordance with techniques disclosed herein together with standard techniques well known to those skilled in the pharmaceutical, medical or veterinary arts. Such compositions can be administered in dosages and by techniques well known to those skilled in the medical or veterinary arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from expression by a vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the inventive adjuvant and optional epitope of interest or antigen may be in admixture with a suitable carrier, diluent, or excipient such as sterile water, physiological saline, glucose or the like.

Antigenic, immunological or vaccine compositions typically can contain an adjuvant; and, the inventive adjuvant comprising insect cells or fractions thereof is well suited for any type of antigenic, immunological or vaccine composition.

Additionally, the inventive immunogenic, antigenic, immunological or vaccine compositions can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the epitope of interest or antigen or, to determine whether an immune response to that agent or to the epitope(s) or antigen(s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference. Uses of monoclonal antibodies are known. One such use is in diagnostic methods, e.g., David, G. and Greene, H., U.S. Pat. No. 4,376,110, issued Mar. 8, 1983, incorporated herein by reference. Monoclonal antibodies have also been used to recover materials by immunoadsorption chromatography, e.g. Milstein, C., Scientific American 243:66, 70 (1980), incorporated herein by reference.

Accordingly, the present invention has numerous utilities.

A better understanding of the present invention and of its many advantages will be had from the following non-limiting Examples, given by way of illustration.

EXAMPLES

Example 1

Insect Cells as Adjuvant for Antigen Favorably Alters Immune Response to Antigen This Example illustrates an embodiment of the invention by showing the property of *S. frugiperda* insect cells to have adjuvant properties that favorably enhance the immune responses to a particular antigen (influenza A/Jalisco/95 H5 hemagglutinin).

A culture of *S. frugiperda* insect cells was infected with a recombinant baculovirus engineered to express avian influenza A/Jalisco/95 H5 hemagglutinin (rHA).

The viral RNA, A/Jalisco/95 (H5N2) is available and was supplied by Dr. Michael Perdue, Influenza Research, ARS, SEPRL, USDA, Athens, Ga. The entire purified viral RNA was used as a template to make cDNA utilizing Moloney Murine Leukemia Virus (M-MULV) reverse transcriptase. The primer used for cDNA synthesis was a synthetic oligonulceotide primer (5'- AGCAAAAGCAGG-3') (SEQ ID NO: 1) homologous to the end of all influenza gene virion segments.

Amplification of the HA gene by polymerase chain reaction (PCR) used Gene Amp kits obtained from Cetus/Perkin Elmer. These 5' and 3' primers were designed with restriction enzyme sites that are not found within the HA genes (Sma1 and Kpn1). The PCR reaction mixture, 100 µl, contained 20 pmol of primers specific for 5' and 3' ends of the H5 HA gene. PCR-amplification was carried out for 25–30 cycles each consisting of 1 min of denaturation at 94° C., 2 min at 35° C. for reanealing and 2 min at 72° C. for extension. The amplified DNA of HA gene was ligated into a transfer plasmid. The resulting double stranded DNA products contained the entire mature HA coding sequence and was verified by DNA sequencing. The HA gene transfer plasmid was then subcloned by standard procedures (Maniatis et al., 1982) into a baculovirus expression vector.

The insect cells containing the selected rHA antigen were harvested by centrifugation, 6,000 rpm for 30 minutes, and vaccine preparations were prepared according to the examples shown in Table 1.

Preparation 1 was whole insect cells that were suspended in phosphate buffered saline (PBS). Preparation 2 was cells suspended in PBS disrupted by mechanical means with a Polytron™ homogenizer (Brinkmann Instruments Inc., Westbury).

Preparations 3 and 4 were insect cells disrupted with a mixture of detergents (see abbreviations to Table 1) selected to inactivate the baculovirus without denaturing the selected antigen. The cells were suspended in the detergent solutions and disrupted with a Polytron™.

Each preparation in Table 1 was analyzed for the presence of infectious baculovirus using a standard baculovirus plaque assay. The hemagglutinin content was measured using a standard chicken red blood cell hemagglutination assay.

TABLE 1

*S. frugiperda* Insect Cells Infected with a Baculovirus Vector Expressing Avian Influenza A/Jalisco/95 H5 hemagglutinin Disrupted with Detergents.

| Prep # | Insect Cells | Treatment |
|---|---|---|
| 1 | Whole | PBS |
| 2 | Disrupted | PBS |

TABLE 1-continued

*S. frugiperda* Insect Cells Infected with a Baculovirus Vector Expressing Avian Influenza A/Jalisco/95 H5 hemagglutinin Disrupted with Detergents.

| Prep # | Insect Cells | Treatment |
|---|---|---|
| 3 | Disrupted | 2% cholate, 0.5% SDS |
| 4 | Disrupted | 2% cholate, 1% CDAB |

Abbreviations:
Prep # - Preparation #;
CDAB - cetyldimethylammonium bromide;
SDS - sodium dodecyl sulfate As a control for the study, influenza A/Jalisco/95 H5 rHA was expressed in *S. frugiperda* insect cells using the baculovirus vector and purified to >95%.

To assess the immunogenicity of the vaccine preparations described in Table 1, aliquots containing equal amounts of rHA as measured using the chicken red blood cell agglutination assay, were injected into groups of six mice. Each vaccine preparation was administered in a 0.5 mL dose, to groups of six mice for each preparation. No immediate or delayed toxic effects, inflammatory responses, or granulomas at the site of inoculation were observed. Lack of toxicity of the preparations was confirmed by the normal weight gain of animals (Table 2).

TABLE 2

The average Weight Gain over 28 Days in Mice Immunized with Vaccine Preparations.

| # | Vaccine Preparation | Weight gain (percent increase) | Standard Deviation |
|---|---|---|---|
| 1 | Whole cells | 19 | 14 |
| 2 | Disrupted PBS | 22 | 6 |
| 3 | 2% cholate, 0.5% SDS | 24 | 9 |
| 4 | 2% cholate, 1% CDAB | 26 | 7 |
| 5 | rHA purified | 16 | 14 |
| 6 | rHA purified + Freund's | 24 | 12 |
| 7 | PBS control | 26 | 11 |

Blood samples were obtained 21 days after injection and the sera analyzed by an enzyme linked immunosorbent assay (ELISA) for the presence of the anti-rHA antibodies. The samples were also analyzed by the hemagglutinin inhibition assay (HAI) for the presence of anti-rHA antibodies that could neutralize the influenza A/Jalisco/95 H5 virus (Table 3).

TABLE 3

Immunogenicity of the influenza A/Jalisco/95 H5 rHA in Mice Immunized rHA Antigen in Insect Cells.

| # | Vaccine Preparation | Antibody Titer 3 weeks | HAI Titer 3 weeks |
|---|---|---|---|
| 1. | Whole cells | 57,470 | 128 |
| 2. | Disrupted PBS | 77,605 | 128 |
| 3. | 2% cholate, 0.5% SDS | 61,440 | 205 |
| 4. | 2% cholate, 1% CDAB | 102,400 | 287 |

TABLE 3-continued

Immunogenicity of the influenza A/Jalisco/95
H5 rHA in Mice Immunized rHA Antigen in
Insect Cells.

| # | Vaccine Preparation | Antibody Titer 3 weeks | HAI Titer 3 weeks |
|---|---|---|---|
| 5. | rHA purified | 10,159 | 29 |
| 6. | rHA purified + Freund's | 102,400 | 645 |
| 7. | PBS control | 10 | 4 |

The data presented in Table 3 shows that the selected antigen, rHA, without an adjuvant (Table 3, preparation #5) produced only a very weak immune response. As expected, the purified rHA mixed with a Freund's complete adjuvant produced a very strong antibody response that included a high level of neutralizing antibodies (Table 3, preparation #6).

When the selected rHA antigen was presented to the immune system as part of the whole or disrupted insect cell its immunogenic properties were significantly enhanced. Whole insect cells, insect cells disrupted with a mechanical process, and insect cells disrupted mechanically in the presence of detergents where all significantly more immunogenic than the purified rHA protein (Table 3, preparations #1, #2, #3, and #4). Vaccine preparations of the selected antigen (rHA) in insect cells produced from 5 to 10 times the titer of anti-HA antibodies as purified rHA (Table 3). The insect cells containing the selected rHA antigen and treated by mechanical disruption in the presence of the detergent mixture containing 2% cholate and 1% CDAB induced an average antibody titer in the mice that is equivalent to the purified antigen plus Freund's complete adjuvant (Table 3, preparation #4).

Example 2

Mechanical and/or Chemical Means to Remove or Otherwise Inactivate Recombinant Baculovirus in Insect Cells for Adjuvant It is conventional to inactivate viruses in certain vaccine formulations containing inactivated or subunit vaccines. Baculoviruses are rapidly inactivated by the detergent treatments described in Example 1 while the selected recombinant antigen rHA was not denatured as measured by the HA assay for biological activity and for the ability of the rHA vaccine to induce neutralizing antibodies (Table 3). *S. frugiperda* insect cells infected with a recombinant baculovirus were suspended in 2% cholate, 0.5% SDS containing buffer and disrupted with Polytron™. The aliquots were taken at times indicated in Table 4 and the baculovirus titer determined by plaque assay method. The data presented in Table 4 and FIG. 2 shows that within the first 10 minutes of treatment, recombinant baculovirus infectivity was reduced to undetectable levels.

Table 4 and FIG. 1.
Inactivation of Recombinant Baculovirus
Using SDS/cholate Treatment of Insect
Cells

| # | Time (min) | Virus titer (pfu/ml) |
|---|---|---|
| 1 | 0 | $8.4 \times 10^8$ |
| 2 | 11 | $<10^2$ |
| 3 | 13 | $<10^2$ |
| 4 | 20 | $<10^2$ |
| 5 | 40 | $<10^2$ |
| 6 | 70 | $<10^2$ |
| 7 | 110 | $<10^2$ |
| 8 | 310 | $<10^2$ |

Example 3

*Spodoptera frugiperda* Insect Cells Subfractionated into Membrane Fraction Containing Membrane Bound Recombinant Proteins and the Fraction Containing Soluble Proteins and Majority of the DNA and RNA Insect cells expressing avian influenza A/Jalisco/95 rHA were obtained as described in Example 1. The cells were disrupted in high ionic strength ethanolamine buffer at pH 9.5 with Polytron™ homogenizer (Brinkmann Instruments Inc., Westbury, N.Y.) and the membrane fraction was isolated by centrifugation. The membrane fraction was separated from adsorbed proteins by washing with the low ionic strength ethanolamine buffer at pH 9.5. This procedure also reduces the baculovirus titer approximately 1000-fold. The remaining baculovirus can be completely inactivated by treating the pellet with 0.5% formaldehyde. Data presented in Table 5 and FIG. 3 show that the baculovirus inactivation is a first order process and that the baculovirus can be completely eliminated by an overnight treatment of the washed rHA-containing membrane fraction with 0.5% formaldehyde. In the course of baculovirus inactivation structural integrity of the rHA was monitored by standardized hemagglutination assay. Only hemagglutinin that is properly folded and assembled into trimers can agglutinate red blood cells and denaturation of the recombinant protein is accompanied by the loss of hemagglutination activity. Hemagglutination activity of the rHA did not decrease which indicates that rHA was not denatured during the baculovirus inactivation (Table 5).

Table 5 and FIG. 2.
Inactivation of recombinant baculovirus
with formaldehyde

| Time (hours) | Virus | rHA Units |
|---|---|---|
| 0.01 | 5.60E+05 | 3000 |
| 1 | 8.00E+04 | 3000 |
| 3 | 7.00E+03 | 3000 |
| 4 | 7.30E+03 | 3000 |
| 5 | 2.00E+03 | 5000 |
| 6 | 1.50E+03 | 5000 |

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. In an immunogenic, immunological or vaccine composition comprising at least one epitope of interest or antigen wherein the improvement comprises the composition comprising a first component comprising the epitope of interest or antigen isolated from a source other than insect cells and a second component comprising an adjuvant comprising insect cells or a fraction thereof, wherein the insect cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens.

2. The composition of claim 1 wherein the at least one epitope of interest or antigen comprises at least one isolated epitope of interest.

3. The composition of claim 1 wherein the at least one epitope of interest or antigen comprises at least one isolated antigen.

4. An immunogenic, immunological or vaccine composition comprising at least one immunologically active component, wherein said immunologically active component consists of an epitope of interest or antigen and as an immunogenicity-enhancing adjuvant, insect cells or a fraction thereof, wherein the insect cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens.

5. The composition of any one of claim 2, 3, or 4 wherein the cells are obtainable from infection of the cells by an insect virus.

6. The composition of claim 5 wherein the insect virus is a recombinant insect virus.

7. The composition of claim 5 wherein the insect virus is a baculovirus.

8. The composition of any one of claim 2, 3, or 4 wherein the insect cells are whole and/or intact.

9. The composition of any one of claim 2, 3, or 4 wherein the insect cells are disrupted.

10. The composition of claim 9 wherein the insect cells are disrupted by mechanical or chemical or both chemical and mechanical means.

11. The composition of claim 5 wherein the virus is inactivated and/or removed.

12. The composition of claim 11 wherein the virus is chemically inactivated.

13. The composition of claim 12 wherein the virus is inactivated by treatment with formaldehyde or treatment with at least one detergent.

14. The composition of any one of claim 1, 2, 3, or 4 wherein the adjuvant includes an insect cell membrane fraction.

15. An immunological, immunogenic or vaccine composition comprising at least one epitope of interest isolated from a source other than insect cells and a separately added adjuvant, wherein the adjuvant comprises insect cells or a fraction thereof, wherein the cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens.

16. A method for eliciting an immunological or protective response in an animal or human comprising administering to the animal or human a composition as claimed in any one of claim 1, 15 or 4.

17. The composition of any one of claim 1, 2, 3, or 4 wherein the adjuvant insect cells are obtainable from a Lepidopteran species.

18. The composition of any one of claim 1, 2, 3, or 4 wherein the adjuvant insect cells are obtainable from *Spodoptera frugiperda*.

19. The composition of any one of claim 1, 2, 3, or 4 wherein the adjuvant insect cells are from the Sf9 cell line.

20. The composition of claim 1 wherein the adjuvant insect cells are obtainable from infection of the cells by an insect virus.

21. The composition of claim 20 wherein the insect virus is a recombinant insect virus.

22. The vaccine composition of claim 20 wherein the insect virus is a baculovirus.

23. The composition of claim 1 wherein the adjuvant insect cells are whole and/or intact.

24. The composition of claim 1 wherein the adjuvant insect cells are disrupted.

25. The composition of claim 24 wherein the adjuvant insect cells are disrupted by mechanical or chemical or both chemical and mechanical means.

26. A kit for the preparation of an immunogenic, immunological or vaccine composition comprising at least one epitope of interest or antigen and an adjuvant, wherein the adjuvant comprises insect cells or a fraction thereof, wherein the cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens; said kit comprising the epitope of interest or antigen in a first container, and the adjuvant in a second container, and optionally instructions for admixing the epitope of interest or antigen and the adjuvant and/or for administration of the composition; and wherein optionally the containers are in a package.

27. The kit of claim 26 wherein the adjuvant insect cells are obtainable from a Lepidopteran species.

28. The kit of claim 26 wherein the adjuvant insect cells are obtainable from *Spodoptera frugiperda*.

29. The kit of claim 26 wherein the adjuvant insect cells are from the Sf9 cell line.

30. The kit of claim 26 wherein the adjuvant insect cells are obtainable from infection of the cells by an insect virus.

31. The kit of claim 30 wherein the insect virus is a recombinant insect virus.

32. The kit of claim 30 wherein the insect virus is a baculovirus.

33. The kit of claim 31 wherein the recombinant insect virus is a recombinant baculovirus comprising at least one exogenous coding nucleic acid for an epitope of interest or antigen.

34. The kit of claim 26 wherein the adjuvant insect cells are whole and/or intact.

35. The kit of claim 26 wherein the adjuvant insect cells are disrupted.

36. A method for enhancing the immunogenicity of an isolated epitope of interest or antigen comprising administering the isolated epitope of interest or isolated antigen with or in conjunction with an adjuvant, wherein the adjuvant comprises insect cells or a fraction thereof, wherein the cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens.

37. The method as claimed in claim 36 further comprising preparing the adjuvant by a method comprising isolating insect cells, and optionally infecting the cells with an insect virus, and optionally disrupting and/or fractionating the cells, and optionally inactivating the virus.

38. The method of claim 36 wherein the adjuvant insect cells are obtainable from a Lepidopteran species.

39. The method of claim 36 wherein the adjuvant insect cells are obtainable from *Spodoptera frugiperda*.

40. The method of claim 36 wherein the adjuvant insect cells are from the Sf9 cell line.

41. The method of claim 36 wherein the adjuvant insect cells are obtainable from infection of the cells by an insect virus.

42. The method of claim 41 wherein the insect virus is a recombinant insect virus.

43. The method of claim 41 wherein the insect virus is a baculovirus.

44. The method of claim 42 wherein the recombinant insect virus is a recombinant baculovirus comprising at least one exogenous coding nucleic acid for an epitope of interest or antigen.

45. The method of claim 36 wherein the adjuvant insect cells are whole and/or intact.

46. The method of claim 36 wherein the adjuvant insect cells are disrupted.

47. The method of claim 46 wherein the adjuvant insect cells are disrupted by mechanical or chemical or both chemical and mechanical means.

48. The method of claim 16 wherein the adjuvant insect cells are obtainable from a Lepidopteran species.

49. The method of claim 48 wherein the adjuvant insect cells are disrupted by mechanical or chemical or both chemical and mechanical means.

50. The immunological, immunogenic or vaccine composition of claim 15 wherein the adjuvant insect cells are obtainable from a Lepidopteran species.

51. The immunological, immunogenic or vaccine composition of claim 15 wherein the adjuvant insect cells are obtainable from *Spodoptera frugiperda*.

52. The immunological, immunogenic or vaccine composition of claim 15 wherein the adjuvant insect cells are from the Sf9 cell line.

53. The immunological, immunogenic or vaccine composition of claim 15 wherein the adjuvant insect cells are obtainable from infection of the cells by an insect virus.

54. The immunological, immunogenic or vaccine composition of claim 53 wherein the insect virus is a recombinant insect virus.

55. The immunological, immunogenic or vaccine composition of claim 53 wherein the insect virus is a baculovirus.

56. The immunological, immunogenic or vaccine composition of claim 15 wherein the adjuvant insect cells are whole and/or intact.

57. The immunological, immunogenic or vaccine composition of claim 15 wherein the adjuvant insect cells are disrupted.

58. The immunological, immunogenic or vaccine composition of claim 57 wherein the adjuvant insect cells are disrupted by mechanical or chemical or both chemical and mechanical means.

59. A method for preparing a composition comprising at least one isolated epitope of interest or antigen and as an immunogenicity-enhancing adjuvant insect cells or a fraction thereof, wherein the insect cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens, said method comprising infecting insect cells with a recombinant insect virus comprising at least one exogenous coding nucleic acid molecule for the epitope of interest or antigen and expressing the epitope of interest or antigen, isolating insect cells, isolating the epitope of interest or antigen, and optionally disrupting and/or fractionating the cells, and optionally inactivating the virus.

60. A method for preparing a composition comprising at least one isolated epitope of interest or antigen and as an immunogenicity-enhancing adjuvant insect cells or a fraction thereof, wherein the insect cells are obtainable from an insect species which is not biting and/or from an insect species wherein hypersensitivity to the insect cell antigens is low or absent in human and animal species and/or from an insect species which is non-toxic, non-pyrogenic, non-tumorgenic, contains no known retroviruses or other human or animal viruses, mycoplasma or other pathogens, said method comprising admixing the adjuvant and the at least one epitope of interest or antigen.

61. The method of claim 16 wherein the adjuvant insect cells are obtainable from infection of the cells by an insect virus.

62. The method of claim 61 wherein the insect virus is a baculovirus or a recombinant baculovirus.

63. The method of claim 16 wherein the adjuvant insect cells are whole and/or intact or are disrupted.

64. The method of claim 63 wherein the adjuvant insect cells are disrupted by mechanical or chemical or both chemical and mechanical means.

65. The kit of claim 35 wherein the adjuvant insect cells are disrupted by mechanical or chemical or both chemical and mechanical means.

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Spodoptera frugiperda

<400> SEQUENCE: 1
agcaaaagca gg                                                              12